United States Patent [19]

Puumalainen

[11] Patent Number: 5,047,723
[45] Date of Patent: Sep. 10, 1991

[54] METHOD FOR DETECTION OF FOREIGN MATTER CONTENTS IN GASES

[76] Inventor: Pertti Puumalainen, Päivärinteentie 3, 70300 Kuopio, Finland

[21] Appl. No.: 286,063

[22] PCT Filed: Jun. 1, 1987

[86] PCT No.: PCT/FI87/00075
§ 371 Date: Dec. 1, 1988
§ 102(e) Date: Dec. 1, 1988

[87] PCT Pub. No.: WO87/07720
PCT Pub. Date: Dec. 17, 1987

[30] Foreign Application Priority Data

Jun. 3, 1986 [FI] Finland .................................. 862349

[51] Int. Cl.⁵ ............................................. G01N 27/62
[52] U.S. Cl. .................................. 324/464; 73/28.02; 324/459; 324/71.3
[58] Field of Search .............. 324/464, 469, 459, 71.3, 324/468, 470, 466, 465, 452; 250/385.1, 379; 340/629; 73/28.02, 23.2

[56] References Cited

U.S. PATENT DOCUMENTS 3,679,973  7/1972  Smith, Jr. et al. .................. 324/464
4,041,376  8/1977  Furuto et al. ....................... 324/469
4,114,088  9/1978  Laws ................................... 324/464
4,724,394  2/1988  Langer et al. ....................... 324/464

Primary Examiner—Kenneth Wieder
Assistant Examiner—Robert W. Mueller
Attorney, Agent, or Firm—Cushman, Darby & Cushman

[57] ABSTRACT

A method for detection of alien matter content in gas, in which the gas and the materials contained in it are ionized in an ionization room (1). The present methods are inaccurate and unreliable. The invention is based on a method, in which the ionized gas is led through chambers (2) containing different electric fields, out of which at least from one of the chambers the field current is measured, from which a signal is obtained, which describes the existence of alien matters in the gas. More parameters are obtained for detection of different materials by measuring favorably the currents passed through several electric field chambers as well as possibly by branching off from the ionization source the flow to different analysis lines of the electric field chambers.

4 Claims, 1 Drawing Sheet

METHOD FOR DETECTION OF FOREIGN MATTER CONTENTS IN GASES

The invention relates to a method for detection of foreign matter in gases, in which method the gas and the foreign matter contained in it are ionized in an ionization zone.

For many different purposes, it is necessary to detect and to measure the contents of foreign matter contained in gases. In particular, when analyzing for very small quantities of foreign matter, the impurities of the gas may disturb the detection. In general, there are problems with the detection of different molecules or molecular groups in gases, as well as in gases attenuated by vacuum pumps or in vapour originating from evaporated solid or liquid materials. In particular there are difficulties in quickly and dependably detecting noxious gases contained in the atmosphere, such as from an industrial accident, or detecting never or other combat gases The principle method used today for analyzing such gases is the EC-detector of gas chromatographs, in which radioactive radiation is allowed to ionize the carrier gas and the molecules of the foreign matter contained in it. The ionized molecules of the carrier gas are permitted partly by means of delay to recombine themselves, after which the ions of the gas are measured. In such manner, for instance, there is obtained a signal indicative of organic substances evaporated into the carrier gas. Measuring devices based on this same principle have also been designed for analyzing nerve gases contained in the air. These devices are of two categories: in the first category the ionized molecules are led into a labyrinth, where the molecules of air are allowed to recombine themselves and the current of ions caused by organic molecules is thereafter measured. In the other category the entery of light air molecules into the ion measuring space is impeded by means of voltage grids. However, the method and the devices for carrying it out are not sufficiently sensitive for measuring low concentrations, such as nerve gases and the like in the air or they give a signal which may include other materials or impurities contained by the air, such as tobacco smoke, exhaust gases, explosion gases, protection smokes etc. Additionally, the a signal may be created by a sudden increase in the moisture content of the air, again giving an inaccurate result.

It is the purpose of the invention is to provid a method for detecting and measuring the quantity and quality of foreing matter contained in a gas. In particular, it is an object of the invention to provide a method of detecting very small amounts of a foreign substance even in the presence of other extraneous material in the gas.

SUMMARY OF THE INVENTION

The present invention in its broadest aspect relates to a method for the detection of foreign matter in gases, in which method the gas containing foreign matter is ionized in an ionization zone. The invention is characterized in that the ionized gas containing foreign matter are passed through chambers with different electric fields, and the field currents passing through two or more chambers are measured, and corresponding signals are obtained. The amounts and relationships of these signals provide an analysis of the foreign matter in the gases. An important feature of the invention is that the moving and recombinating ability of different molecules is taken advantage of in different electric fields, when the whole of the gas has initially been ionized in the ionization zone.

The method of the invention can be operated under atmospheric pressure or under vacuum. The method can also be used in many different chemical analyzing methods, such as in a detector of a gas chromatograph or in a detector of a liquid chromatograph, in which the materials are first heated or brought into a gaseous state by lowering the pressure. In such a way, the analyses may be carried out with higher resolution. With the help of the method in accordance with the invention it is also possible to measure concentrations from a desired group of materials and additionally divide the group into subdivisions, for instance in order to determine the characteristic of the nerve gas.

It is particularly favourable according to the invention to pass the ionized gas containing foreign matter through at least two adjacent channels, each such channel containing at least one of the electric field chambers. The field current passing through at least one chamber of each channel is measured and a signal based on each field current measurement is obtained. The amounts and relationships of these signals obtained provide the desired analysis of the foreign matter.

In the following the invention is explained more in detail

According to a further preferred embodiment, the ionized gas containing foreign matter is passed along a tortuous path within each electric field chamber. this tortuous path being defined by current measuring plates extending inwardly from the walls of the chamber, with a gap between each measuring plate and the chamber wall defining at least two electric field sub-chambers within each chamber. The intensity of the electric field in the sub-chambers are different from each other.

Certain preferred embodiments of this invention are illustrated in the attached drawings, in which:

FIG. 1 is a schematic cross-section of one method for carrying out the invention; and FIG. 2 is a schematic cross-section of an alternative method for carrying out the invention.

DESCRIPTION OF THE PREFERRED EMBODIMENTS:

Figure 1:
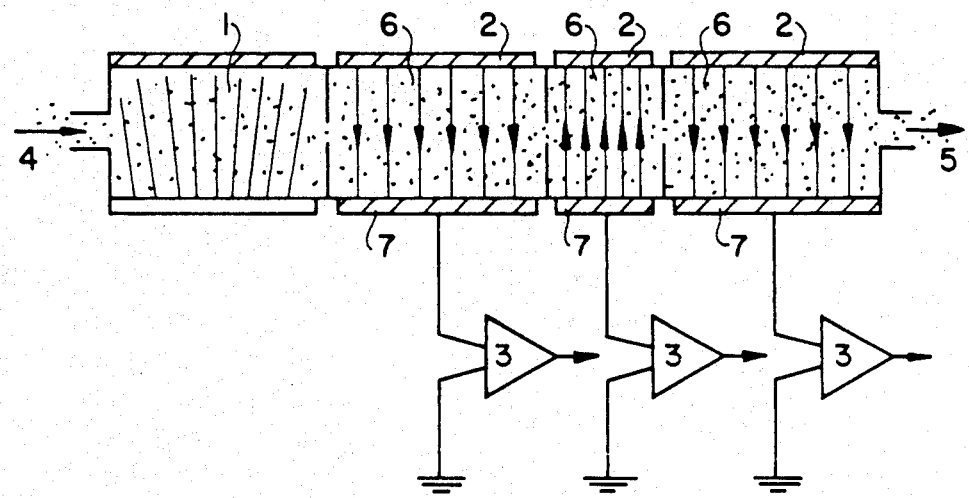

In the in FIG. 1 presented application the principle of the method in accordance with the invention has been presented. To the device system belong the ionization room 1, the chambers 2 and the meters 3. Into the chambers 2 has been formed with the voltage plates the traverse electric fields 6 of different magnitude. In the ionization room a suitable radio isotope is used, with the help of the radiation of which the ionization of the gas is taking place. The gas to be examined is brought in this application in by suction through the intake opening 4 to the ionization room 1 and from there the ionized gas is led through the chambers placed after each other through the outfeed opening 5 out of the device system. The flow is obtained in this application by means of an air pump, by which the gas and its components are sucked through the analyzing device system. In the ionization room the ionized molecules and the fragmented molecules are transported through the chambers and through the different electric fields existing in the chambers. Hereby the molecules endeavour to recombine themselves or to destroy their charges and in the different electric fields also iones are removed from the system. In the figure the voltages form together with the earth coupled lower plates field lines into the passage space, and when the intensifiers 3 are coupled to the ground current, it is possible to start treating the signal. By setting two or more flowing measurings in the same flowing channel can at using of electric field of different magnitude different molecule groups be separated from each other with the help of typical flow signals from different spots. By observing the flow signal values characteristic for each molecule group the observation and measuring result is obtained.

Figure 2:
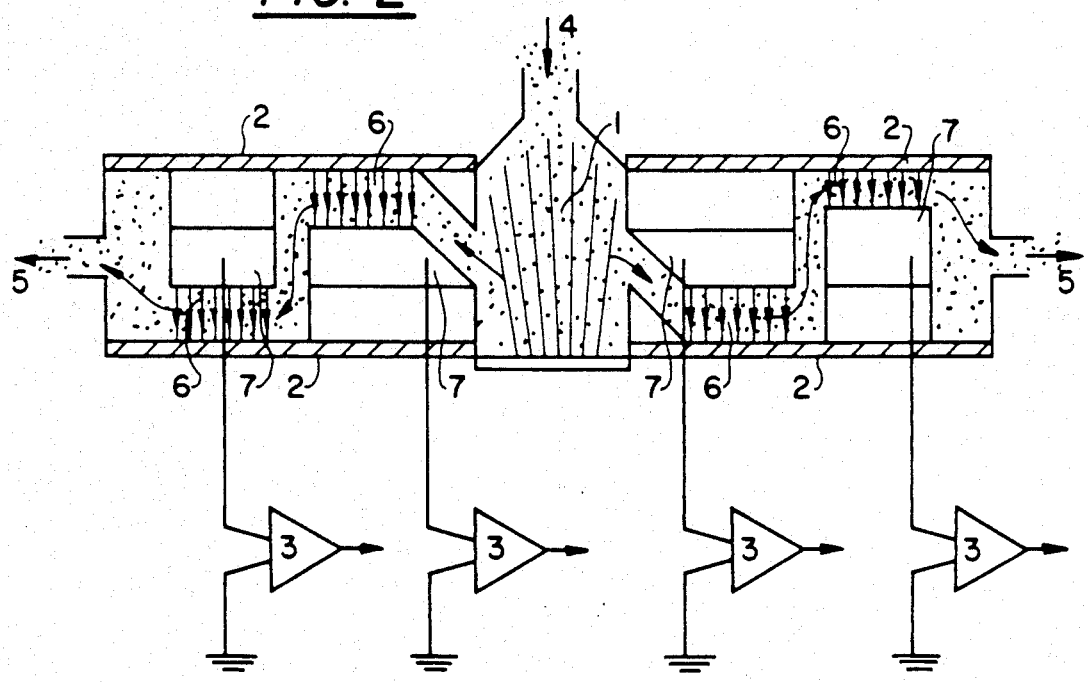

In the application presented in FIG. 2 the ionization room 1 is in the middle of a mainly sheet-formed body, where the chambers are placed on both sides of the ionization room side by side. To the ionization room several chambers are connected radially or at least channels formed by one chamber. In this application the walls of the chamber are formed by the voltage plates 2 and between the voltage plates the measuring plate 7 is placed. The measuring plate is divided into parts and placed between the voltage plates in such a manner, that the distance between it and the voltage plates varies. Hereby has between the voltage plates been formed at least 2 minor chambers, the electric field intensity vary from each other. The gas to be examined is led out from the ionization room by changing the route of the gas on the different sides of the measuring plate by taking advantage of the openings in the measuring plate. The parts of the measuring plate are fixed to the one of the voltage plate. From the measuring plates the current is measured against the ground with the help of the intensifiers 3. From the ionization room leave several measuring channels (on the figure two channels) and the voltage plates are in different potentials in regard of the measuring plate 7. Hereby it is possible to start measuring signals right after the ionization, for instance in opposite electric fields against the ground. The alien matter content can be detected and measured by leading ionized gas into the channels of the device system, in which there are chambers with different electric fields, and by measuring the through the chambers passing field current the measuring values are obtained.

One advantage of the structure presented in FIG. 2 is, that the measuring spots can be made for instance directly on the electronic circuit card and the voltage plates are on top of the insulations acting as protective sheets for the structure. With the help of this kind of a two-channel analyzer it is possible to measure concentrations of nerve gases, which are below even 0.1 mg/cu.m, when usually as an alarm limit for instance for sarine is considered 0.5 mg/cu.m. The false signals caused by tobacco smoke, combustion gases, explosion gases and protection smokes can be eliminated with this kind of multimeasuring.

The invention is not limited to the presented favourable application modes, but it can be transformed within the frames of the attached patent claims. The invention is not connected only with the analyzing of the nerve gases from the air, but ir can be used for detection and analyzing of different molecules and molecule groups performed from gas in general, from gas attenuated with the help of a vacuum pump as well as from vapour of evaporized solid or liquid substances.

I claim:

1. A method for detecting foreign matter in gases, comprising the steps of:
   ionizing the gas containing foreign matter in an ionization zone,
   passing the ionized gas containing foreign matter through a plurality of chambers, each with different electric fields,
   measuring field currents passing transversely through two or more of said chambers, and
   obtaining corresponding signals, wherein amounts and relationships of said signals provide an analysis of the foreign matter in the gases.

2. A method according to claim 1, wherein said step of passing the ionized gas containing foreign matter through chambers comprises passing the gas through sequentially arranged electric field chambers.

3. A method according to claim 1, wherein said step of passing the ionized gas containing foreign matter comprises passing the gas through at least two adjacent channels, each of said channels containing at least one of said electric field chambers, the field current passing through at least one chamber of each channel being measured and a signal based on each field current measurement being obtained.

4. A method according to claim 1, wherein said step of passing the ionized gas containing foreign matter comprises passing the gas along a tortuous path within each of said chambers, said tortuous path being defined by current measuring plates extending inwardly from walls of the chamber, with a gap between each measuring plate and chamber wall defining at least two electric field sub-chambers within said chamber, an intensity of an electric field in each said sub-chamber being different from one another.

* * * * *